US012740818B2

(12) United States Patent
Crook et al.

(10) Patent No.: US 12,740,818 B2
(45) Date of Patent: Sep. 22, 2026

(54) METHOD, DEVICE, AND SYSTEM FOR PRE-BIASED TISSUE WITH LOWER-ENERGY IRREVERSIBLE ELECTROPORATION AND TISSUE IDENTIFICATION FOR PULSE FIELD IMMUNOTHERAPY

(71) Applicant: OSO MEDICAL, INC., Belmont, CA (US)

(72) Inventors: Jeffery Crook, Belmont, CA (US); Paul Friedrichs, Belmont, CA (US); Rohit Chandrakant Mane, Campbell, CA (US); Nastaran Alinezhadbalalami, Alameda, CA (US); Denise Demarais, San Jose, CA (US)

(73) Assignee: OSO MEDICAL, INC., Belmont, CA (US)

( * ) Notice: Subject to any disclaimer, the term of this patent is extended or adjusted under 35 U.S.C. 154(b) by 0 days.

(21) Appl. No.: 18/927,419

(22) Filed: Oct. 25, 2024

(65) Prior Publication Data

US 2025/0134572 A1 May 1, 2025

Related U.S. Application Data

(60) Provisional application No. 63/594,641, filed on Oct. 31, 2023.

(51) Int. Cl.
*A61B 18/18* (2006.01)
*A61B 18/00* (2006.01)
(Continued)

(52) U.S. Cl.
CPC .............. *A61B 18/00* (2013.01); *A61N 1/327* (2013.01); *G16H 20/40* (2018.01);
(Continued)

(58) Field of Classification Search
CPC .......... A61B 18/00; A61B 2018/00613; A61B 2018/00642; A61B 2018/00696;
(Continued)

(56) References Cited

U.S. PATENT DOCUMENTS 7,627,373 B2 * 12/2009 Girouard ................ A61N 1/362 607/9
2002/0193784 A1 * 12/2002 McHale ............ A61K 41/0028 606/41

(Continued)

OTHER PUBLICATIONS

International Search Report and Written Opinion, Application No. PCT/US2024/053045, dated Mar. 14, 2025.

*Primary Examiner* — Michael F Peffley
*Assistant Examiner* — Amanda L Zink
(74) *Attorney, Agent, or Firm* — Merchant & Gould P.C.

(57) ABSTRACT

Several new inventions are detailed with this system, method, and device. While at the core, these inventions may ablate tissue by application of a short duration electric field, the therapy waveform used to apply the electric field is novel and optimized to preserve the intra-cellular content possible across different identified tissues. The optimized pulse biases tissue to an electroporation state and then presents a “hammer pulse” which may be along the same polarity or different polarity. This treatment minimizes thermal effects and is being defined as Pulse Field Immunotherapy (PFI). The antigens are left in situ and taken up by antigen-presenting cells in the periphery allowing the immune system to engage. Additional tissue feedback is obtained through an invention that performs measurements on tissue to determine its composition while the applicator is inserted into normal tissue, followed by diseased tissue. Tissue composition is compared against a library of characterized Tissue Identity Profiles (TIPs), allowing for immediate (Continued)

assessments and therapy to be provided while the patient is undergoing traditional diagnosis.

25 Claims, 12 Drawing Sheets

(51) Int. Cl.

| | |
|---|---|
| ***A61B 18/12*** | (2006.01) |
| ***A61N 1/32*** | (2006.01) |
| ***G16H 20/40*** | (2018.01) |

(52) U.S. Cl.
CPC ............... *A61B 2018/00613* (2013.01); *A61B 2018/00642* (2013.01); *A61B 2018/00696* (2013.01); *A61B 2018/00732* (2013.01); *A61B 2018/00767* (2013.01); *A61B 2018/00904* (2013.01)

(58) Field of Classification Search
CPC .......... A61B 2018/00732; A61B 2018/00767; A61B 2018/00875; A61B 2018/00904
See application file for complete search history.

(56) References Cited

U.S. PATENT DOCUMENTS

| | | | | |
|---|---|---|---|---|
| 2008/0071265 | A1* | 3/2008 | Azure | A61B 18/1477 606/41 |
| 2014/0378964 | A1* | 12/2014 | Pearson | A61B 18/1477 606/41 |
| 2017/0105793 | A1* | 4/2017 | Cao | A61N 1/325 |
| 2017/0348525 | A1 | 12/2017 | Sano et al. | |
| 2018/0168727 | A1* | 6/2018 | Lin | A61N 2/002 |
| 2019/0117964 | A1* | 4/2019 | Bahrami | A61N 1/327 |
| 2019/0336757 | A1* | 11/2019 | Rodriguez | A61N 1/0412 |
| 2021/0052882 | A1 | 2/2021 | Wasson et al. | |
| 2021/0393312 | A1* | 12/2021 | Davalos | A61B 5/0536 |
| 2025/0292904 | A1* | 9/2025 | Wolber | G16H 20/10 |
| 2025/0339091 | A1* | 11/2025 | Ghramh | A61B 5/445 |

* cited by examiner

METHOD, DEVICE, AND SYSTEM FOR PRE-BIASED TISSUE WITH LOWER-ENERGY IRREVERSIBLE ELECTROPORATION AND TISSUE IDENTIFICATION FOR PULSE FIELD IMMUNOTHERAPY

TECHNICAL FIELD

The present disclosure relates to the medical field and, in particular, relates to an electroporation device configured to deliver irreversible electroporation signals in a manner that optimally preserves the released antigens, along with a complex sensing device that examines cellular identities to further improve tissue confidence and applicators for joint sensing/delivery of therapy.

BACKGROUND

Several cancers have a low probability of survival—one of the worst ones is pancreatic cancer. Pancreatic cancer has a 10% survival rate after year 5 and is the fourth leading cause of cancer death in the USA.

Since early-stage pancreatic cancer often has no noticeable signs or symptoms, it is usually not detected until it has spread and metastasized to other tissues or organs, leading to various symptoms. Once the cancer spreads, it becomes increasingly difficult to treat, contributing to the very high mortality rate. Approximately half of all cases detected have progressed to stage 4—a distant, or metastatic diagnosis. At this late (advanced) stage, the cancer has spread beyond the initial localized tumor (regional phase) and into other remote tissues (metastatic phase), such as lymph nodes or other organs and the patient is presenting with other symptoms.

Diagnostic tools include imaging or surgical techniques such as computed tomography (CT), magnetic resonance imaging (MRI), and fine needle aspiration (FNA). When detected, most cases are already in the metastatic phase, leaving few options for treatment. Systemic chemotherapy is the current standard of care, but is largely palliative in nature, marginally prolonging life but with significant side effects and diminishing quality of life. Systemic immunotherapy provides alternative treatment options; however, it requires specific targeting and is highly dependent on the mutation burden of the tumor and hence is only effective for a small percentage of pancreatic cancer patients. Local drug delivery is also under investigation as a means to provide therapy with reduced toxicity; however, these therapies are only useful if the cancer is detected early (i.e., regional phase). When surgery is performed (only about 20% of pancreatic cancer patients qualify), the primary surgical technique is the Whipple Procedure (also called a pancreaticoduodenectomy) which is a complex and costly surgery involving removal of the head of the pancreas, most of the duodenum (a part of the small intestine), a portion of the bile duct, the gallbladder and associated lymph nodes.

Energy-delivery techniques have also been attempted, either alone or in combination with systemic or local drug delivery. Thermal ablation techniques (e.g., radiofrequency) have showed limited efficiency due to the highly vascularized nature of the pancreatic tumors and the heat sink effects associated with thermal ablations. There has been some evidence of a systemic immunological response with thermal ablation techniques due to the induced cellular damage, however the extent of such immunological response has been limited. A systemic immunological response is highly desirable, as the body may now attack cancer cells not only in the regional phase but also in the distant metastatic phase. Unfortunately, this effect is very limited with thermal ablation techniques, due to the thermal damage on the cellular proteins that play an important role in initiation of an immune response (i.e., including the intracellular components responsible for triggering a systemic immunological response).

High voltage pulsed electric fields have been used to manipulate target cells (reversible electroporation) to deliver therapeutic agents, but the delivered agents (e.g., chemotherapy) are designed to kill the cancer cells, including the intracellular components, thereby significantly reducing or eliminating the potential for a systemic immunological response. High voltage pulsed electric fields have also been used to directly cause cell death (irreversible electroporation) at relatively low temperatures. While this process has the potential to maintain internal cell structures needed to trigger a systemic immunological response, the need to generate large lesions has led to waveforms that cause both athermal and thermal injury that affects the intra-cellular component, again limiting the immunological response.

The current approaches apply the same energy delivery waveform regardless of cancer type, with the goal of maximizing lesion size. However, there are a variety of pancreatic cancer types comprised of different cell types, sizes, or other characteristics. In an effort to minimize thermal effects without compromising lesion size, it would be very beneficial to identify the cancer type and apply a specific energy-delivery waveform designed to optimize the immunological response.

Therefore, there is a need for improved methods, devices, and systems that enable minimally-invasive application of energy waveforms designed to optimize local tumor cell death for malignant cancers (e.g. pancreatic, lung, breast, liver, stomach, ovarian, prostate, etc.) or benign tumors (e.g. brain, spinal cord, etc.) while maximizing release of in-tact intra-cellular components in an effort to cause a systemic immunological response sufficient to eradicate both any remaining local cancer and the metastatic phase of pancreatic cancer, thereby extending patient's lives.

SUMMARY

The present disclosure describes a system that may invoke an improved immune systematic response to fight against diseased tissue (e.g., malignant tissue/cancer, benign tumors). Through use of electrodes with varying placements and a novel electrical pulse pattern, a novel tissue identification method, an optimized irreversible electroporation (IRE) may be achieved to specifically target the membrane while minimizing the intracellular effects, allowing for Pulse Field Immunotherapy (PFI) to ensue.

Tissue identification is performed through a complex measurement pulse with varying frequencies, allowing for a Tissue Identity Profile (TIP) to be resolved. The PFI waveform initially provides a pre-biased pulse pattern, based on the identified tissue cells, to approach the boundary of electroporation. Once the cells are weakened (have pore formation), they may more readily breakdown and the PFI pulse transitions to apply a higher amplitude pulse with a shorter duration, herein referred to as a "hammer pulse". The hammer pulse may be on the same electrodes, or physically have a different electric field gradient and vector (from different electrodes) which may stress the cell membrane further until lysing occurs. This may minimize intracellular thermal damage, which inversely correlates to maximizing an immune response. The hammer pulse changes through the TIP, optimizing the therapy. The optimized PFI pulse may also allow for minimizing pulse intensity and overall energy delivery to minimize muscle contractions during therapy as compared to existing pulse field ablation (PFA) therapies, eliminating the need for paralytics and synchronization of the PFI pulse to the patient's cardiac cycle. The concept parallels priming the cellular structure into a more vulnerable state, which is novel, then forcing a larger stress onto the cell membrane (IRE), perhaps with a different electrical field gradient and/or vector, making it rupture under deliberate strain.

Evoking an immune response provides a better way for the human body to engage cancer on both a macroscopic and microscopic level. This opens the possibility of not using traditional cancer treatments such as high-risk surgical resections, chemotherapy, radiation therapy, etc. that place a huge stress on the human body. A whole-body immunological response may also open the possibility of increased survival for Stage 4 cancer patients that have few or no options left for treatment.

PFI could also show benefit when used in combination with other emerging therapies such as checkpoint inhibitor drugs, chemotherapy drugs, or RenovoRx's therapy platform for all cancers, RenovoTAMP® currently in clinical studies for the treatment of locally advanced pancreatic cancer (LAPC).

PFI in combination with an additional invention of characterizing multiple tissues across several measurements (e.g., amplitudes and frequencies) allows for Tissue Identity Profiles (TIPs) to be created, enabling the detection of specific tumor types, normal tissue, or already treated tissue, and then utilizing optimized PFI waveform to maximize the antigens left in situ. This may optimize the immune systems signals that cells are not appropriately replicating and need to be attacked by the body's immune system.

Along with increased antigens left in situ through PFI, a further optimization may include local immune cell activation through electrical pulses or activation of the vagus nerve, which increases cell activity, thereby increasing the likelihood of creating and/or enhancing an immune response.

TIPs may be generated through multiple avenues: varying frequency of impedance measurements, capacitance, and voltage levels will help build complex models of how different tissues are 'trained' within our sensing technology system. This extends beyond most systems simple use of impedance to confirm patient resistances and good connection with the electrode. Measurement levels may be calculated to the micro ($10^{-6}$) level (or larger, or smaller) as well as varying frequencies and phases to create minute detectable changes between different tissue types (connective tissue, epithelial tissue, muscle tissue and nervous tissue). The TIPs may be able to distinguish between healthy tissue vs malignant tissue. Additional embodiments to aid in TIPS may include using optical coherence tomography (OCT) alone or with the aforementioned electrical measurement techniques. TIPs could be cloud based with a machine-learning element (i.e., artificial intelligence) involved with the characterization and categorization of different tissue profiles.

Signal processing for TIP creation may include performing convolutions against normal vs. diseased tissues, different frequencies, voltages, capacitances, OCT, and more. A deep organs' localized blood oxygen level measured in vivo via OCT may further help shape the progression and tissue identity profile. Complex scenarios can establish valuable insight into disease identification that may rapidly provide confidence that tissue is malignant, will be malignant, or conformation that it is benign. This may provide a novel approach as early as possible (during tumor assessment) previously unavailable to clinicians/practitioners—and in many cases earlier detection and treatment is key to improving patient outcomes.

The present disclosure may be embodied in other specific forms without departing from the spirit or essential attributes thereof. This disclosure encompasses all combinations of the different aspects of the disclosure noted herein. It is understood that any and all embodiments of the present disclosure may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment. While particular embodiments have been described, it is not intended that the disclosure be limited thereto, as it is intended that the disclosure be as broad in scope as the art will allow.

BRIEF DESCRIPTION OF THE DRAWINGS

Subject matter hereof may be more completely understood in consideration of the following detailed description of various embodiments in connection with the accompanying figures, in which.

Figure 1:
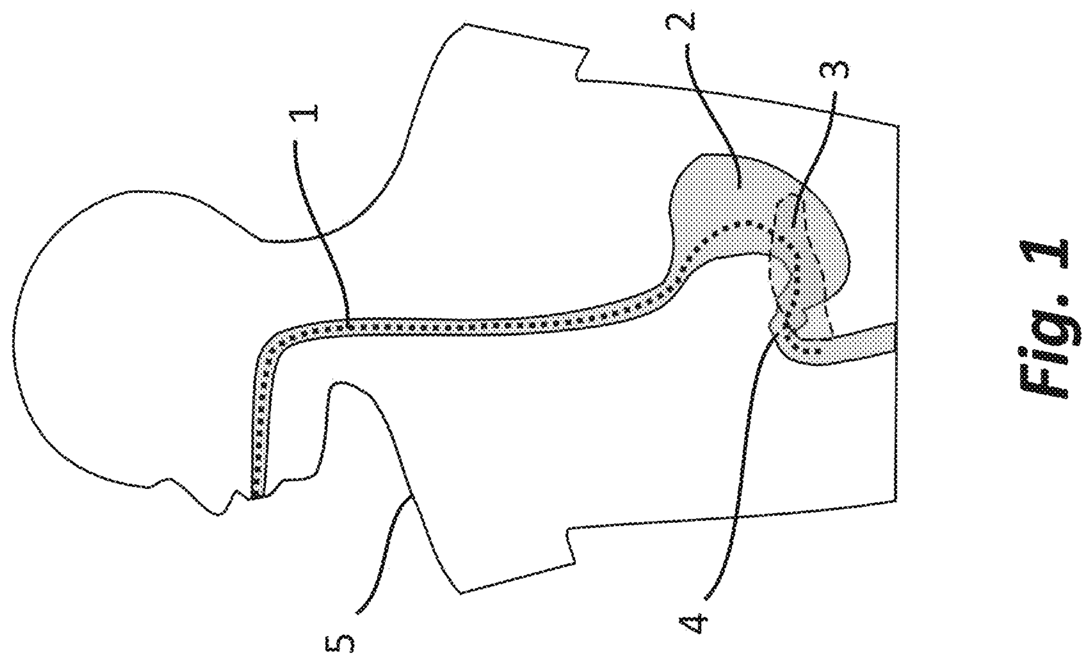
FIG. 1 depicts a human model patient with a cross-sectional view showing access to the pancreas.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

FIG. 1 depicts a human model patient 5 with a cross sectional view showing access to the pancreas 3. Access is provided through the throat down to the stomach 2. A probe is not shown in this example, however, the path a probe would take is shown in the dotted line 1. The probe path moves beyond the stomach 2 into the duodenum), and gains access to the pancreas 3 through the ampulla of Vater and pancreatic ducts, or other standard access methods.

Figure 2:
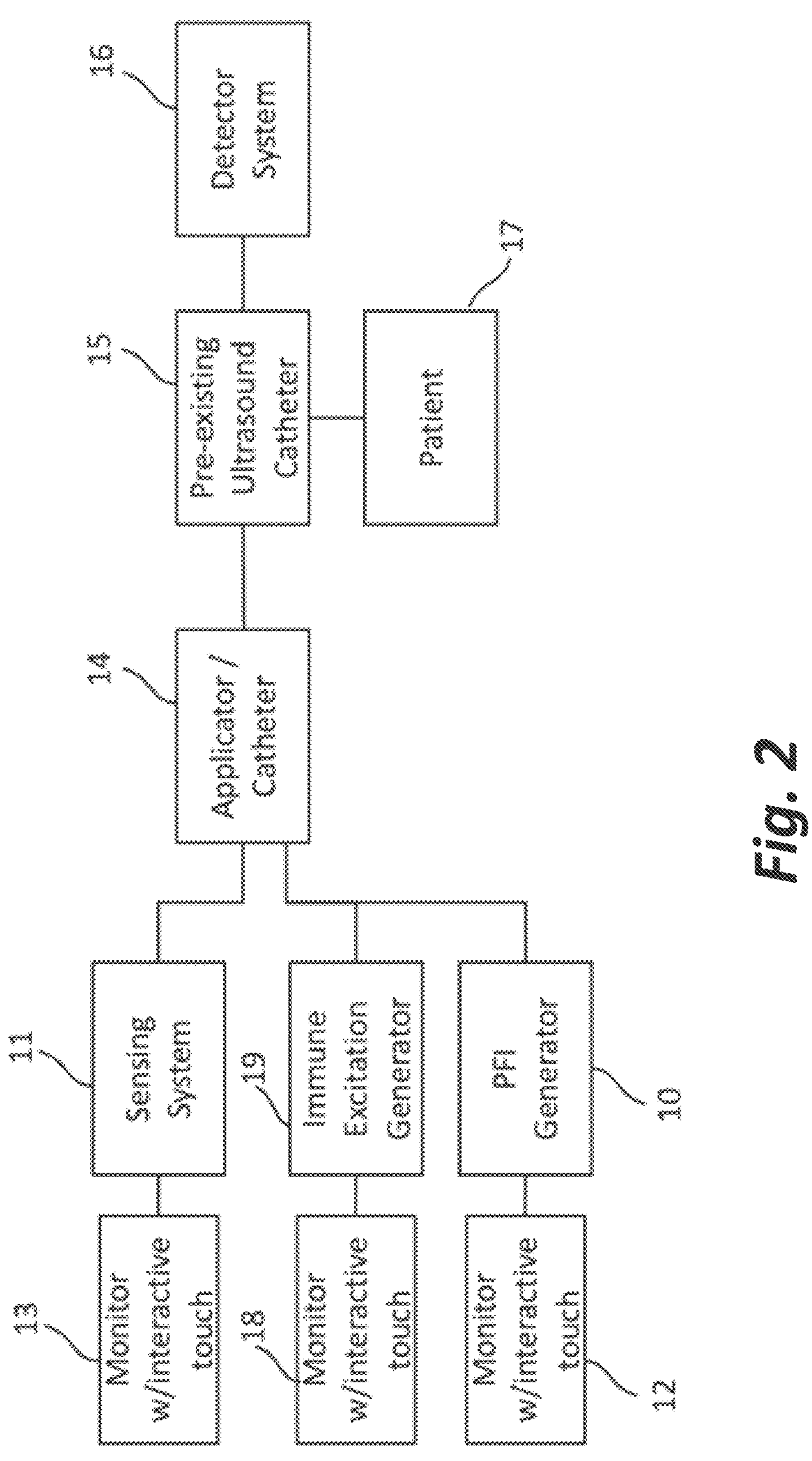
FIG. 2 depicts a system diagram of various embodiments to accomplish a Pulse Field Immunotherapy (PFI) system according to the disclosure.

FIG. 2 depicts a system diagram of various potential embodiments to accomplish a Pulse Field Immunotherapy (PFI) system. The PFI generator 10 is capable of generating the pulse that passes electrical signals through the Applicator/catheter 14. The PFI generator 10 may have a monitor with optional interactive touch 12, to show what the generator is doing (among other things). Signals emerging from the PFI generator leverage may combine with an ultrasound catheter or sonic endoscope to gain access to the patient 17. Other embodiments for different cancer types may be employed with other detection means. A detector system 16 may be used with the ultrasound catheter 15 to look for proper placement of the applicator for a given patient 17. The Tissue Identity Profile (TIP) sensing system 11, with a monitor and interactive touch 13, may enable the clinician to gain immediate feedback of the tissue types that are being detected as the applicator starts within the intestine and moves through a workflow. The Immune Excitation Generator 19, with a monitor and interactive touch 18, sends pulses through the catheter to activate local immune cells.

Figure 3:
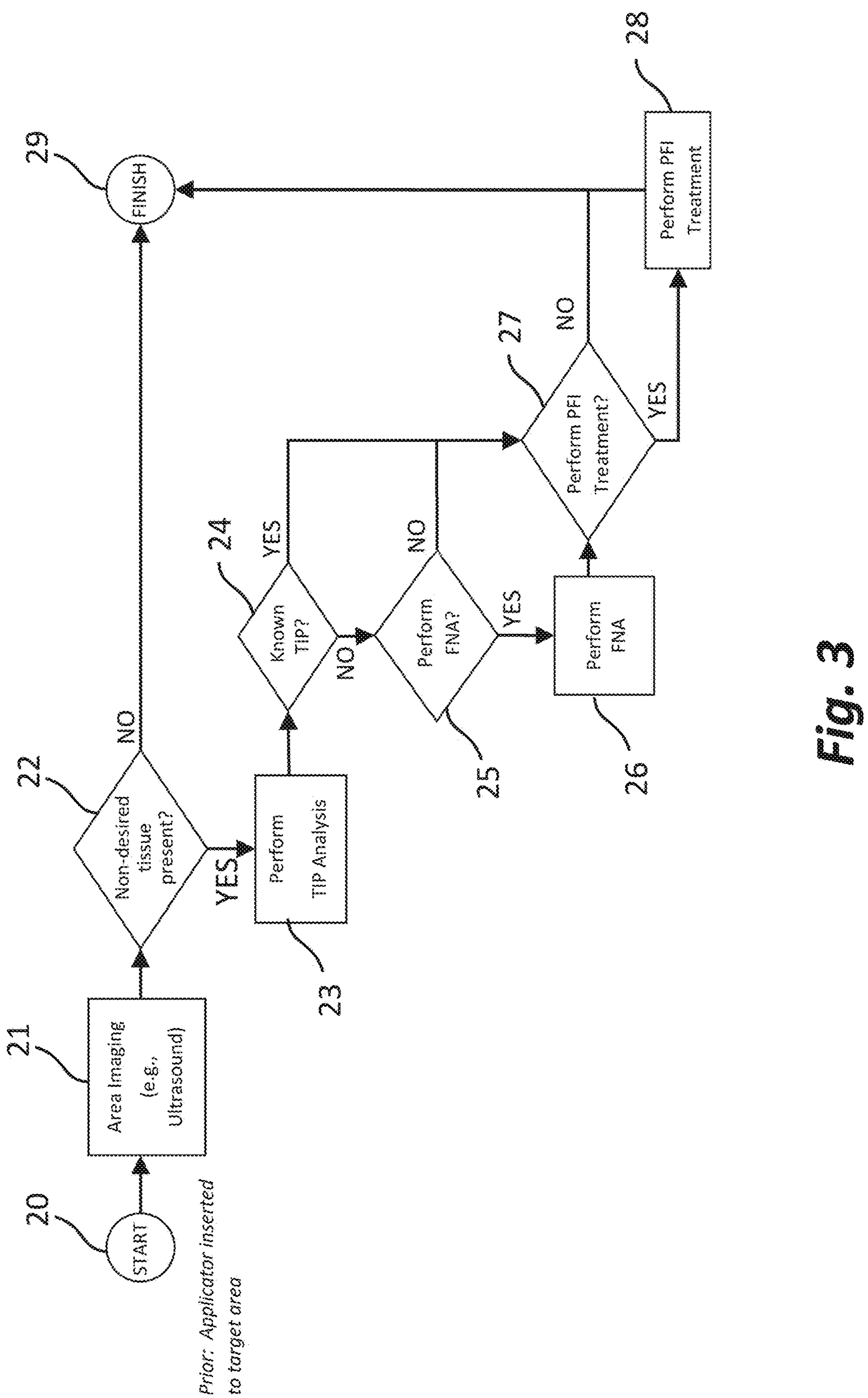
FIG. 3 depicts a method for determining therapy treatment according to the disclosure.

FIG. 3 depicts a method with a starting place 20 that allows for a standard surgery workflow to that point. The sensing area is reached with the ultrasound 21 and an assessment is made 22 analyzing appropriate imaging techniques if non-desired tissue is present. If not present, the practitioner may opt to end the procedure 29 or proceed to perform the novel sensing analysis (TIP) 23 for tissue identification. If the tissue cannot be identified 24, the practitioner has the option of performing fine needle aspiration (FNA) 25. If the tissue can be identified, the practitioner can proceed to perform a PFI treatment 27. This is a novel method and non-obvious providing the benefits of not having to perform FNA on the patient with the associated biopsy analysis time allowing for a real time identification of the tissue as covered later in this embodiment. If performing an FNA 26, the practitioner can use the results from the FNA to decide to perform the PFI treatment 27. If a PFI treatment is performed 28, post treatment the procedure finishes 29.

Figure 4:
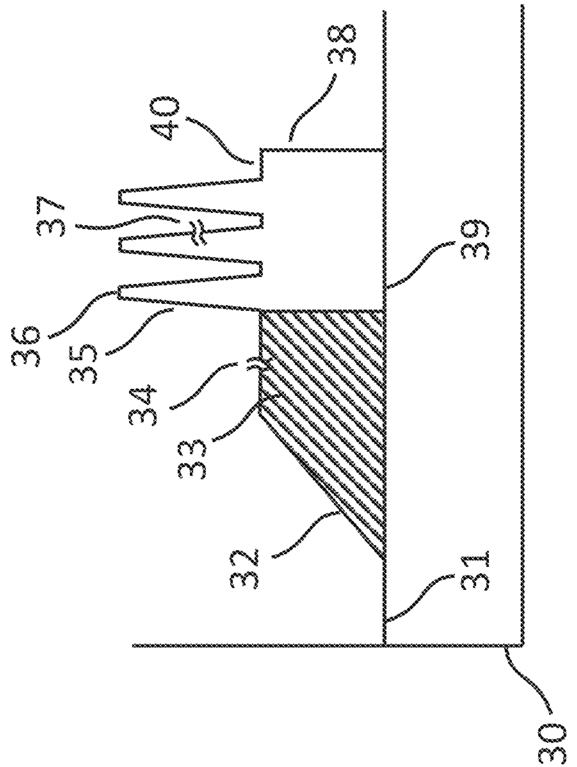
FIG. 4 depicts a novel PFI waveform with various modifications and alternative shapes according to the disclosure.

FIG. 4 depicts an exemplary PFI waveform according to the disclosure with various modifications and alternative shapes with the key elements to be highlighted below. The figure is on a time-series plot 30, with the X axis being time and the Y axis being voltage. This may be translatable into a figure that shows the field being generated over distance in some alternative form (the X axis is still time, however, the Y axis is voltage per centimeter, for example). The start of the pulse 31 is a balanced voltage of 0V. The waveform starts 32 with an acceptable range of slew rate (dv/dt) that aligns with targeting the cell membrane. The waveform then transitions into a bias level 33, allowing for electroporation to occur. The level of the bias 33 can be tuned specifically to achieve larger or smaller volumes of electroporation. The duration 34 is lengthened to collect/recruit as many targeted cells as possible—this is a key novel step to achieve PFI by passing intentionally through a reversible electroporation state. In some cases, items 34 and 40 (or exclusively one or the other) may be desirable zones to apply local immune cell activation through additional electrical pulses or activation of the vagus nerve. The zero-crossing of the PFI pulse 39 is shown as an example, however, the waveform may be reversed with negative polarity. The final portion of the cycle is then entered in which a small series of 'hammer pulses' 35 are applied to the targeted tissue zone. The bias pulses transition to the hammer pulses while still under bias. These hammer pulses may be on the same electrodes, different electrodes within the same plane, or electrodes off of the main bias pulse plane (creating a different targeted electric field vector/angle to the cells). Hammer pulses may occur on different electrodes with the original bias pulse still applied—this novel approach is intended to put the cell membrane under further strain. Hammer pulses may range from one or more—three 35 are shown in FIG. 4. Hammer pluses may be inverted in polarity (i.e., inverted irreversible electroporation). According to various embodiments, some or all of these features may be present in a given waveform.

The characteristics 36 of the pulse can vary in amplitude, offset, frequency, and/or number of pulses 37. The PFI waveform ends 38 by returning to a neutral state. The hammer pulses are of significant novel functionality as they may push the target cell membranes into irreversible electroporation. They may also push volumetrically beyond the reversible electroporation range into new tissue, exposing the new tissue to lysing. Once the reversible electroporation cells have returned to normal (or have electrically been reverted), different volumes can be targeted with amplitude to minimally heat and damage the intracellular content (critical for PFI). Cells may reverse the process of electroporated cells by inversing the bias waveform across the zero-volts axis 39 to speed the therapy process.

Figure 5:
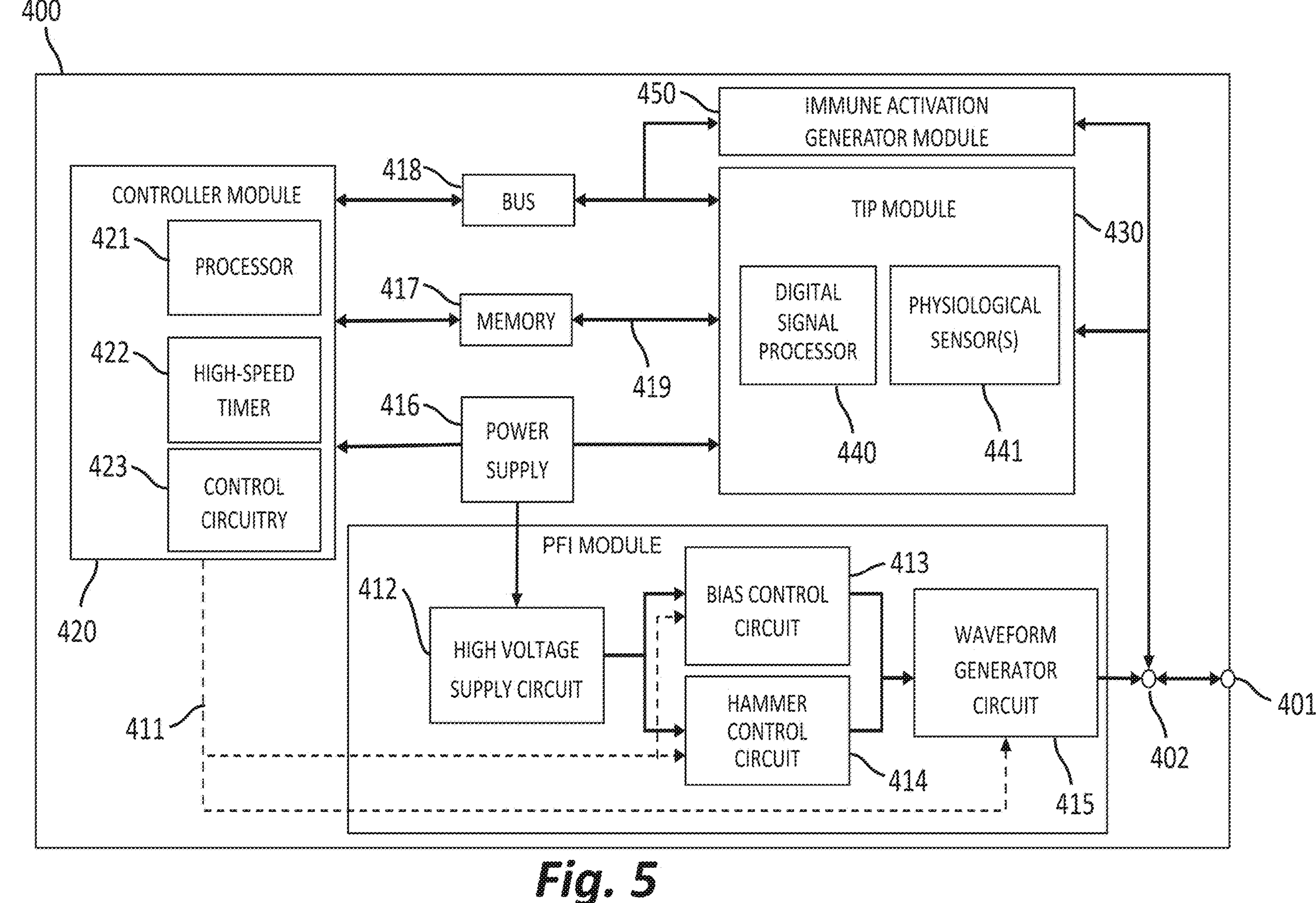
FIG. 5 depicts a block diagram of one possible embodiment of a PFI system that according to the disclosure.

FIG. 5 depicts the block diagram of one possible embodiment of the PFI system 400 that includes the PFI module 410, the controller module 420, the immune activation generator module 450, and the TIP module 430. The PFI module includes a high voltage power supply 412, the bias control circuit 413, the hammer control circuit 414, and the waveform generator circuit 415. These blocks are controlled through a controller module 420 through communication buses, general purpose input/output (GPIO), or other signals 411. The controller module 420 has one possible embodiment of a processor 421 that performs the computing, a high speed timer 422 that performs tracking/switching of fast signals, and the control circuitry 423 that contains several potential functions depending on the embodiment, such as real-time clocks, optical isolators, signal filtering, voltage level shifting, and/or other analog/digital circuitry that may enable the application. Some embodiments of the high-speed timer may use a field programmable gate array (FPGA) or programmable logic device (PLD) to accomplish high resolution timing. A bus 418 from the control module connects to the TIP module 430, allowing for data to be exchanged for several potential purposes such as feedback, algorithms controlling the PFI waveform, and/or verification of the current probe status. Shared memory 417 may also be used, potentially with Direct Memory Access (DMA), allowing for the TIP module to continuously update a sessions data stream without overloading the control module's main processor thread. The power supply 416 supplies power across all modules within the PFI system. The TIP module (tissue identification module) may embody several different functions that enable tissue identification, calibration, and filtering specific to the PFI application enhancement. A digital signal processor 440 enables fast calculations that will help with tissue identification. Physiological sensors 441 enables both signal processing and further extraction of exact tissue identification and may include signal driving and conditioning to support the identification process. A mixer 402 combines signals from the PFI module 410 as a PFI signal generator with the TIP module 430 as a complex impedance, capacitance and other sensor generator. Analog data may be asynchronous or synchronous and both input and output in nature, passing through the device ports 401. The novel implementation of the device extends beyond the PFI waveform generation and into the combination of tissue identity (via the TIP module) within the system, blending an immediate assessment and therapy device, allowing for adjustments to the feedback algorithm based on patient impedance and targeted (identified) diseased cells.

Figure 6:
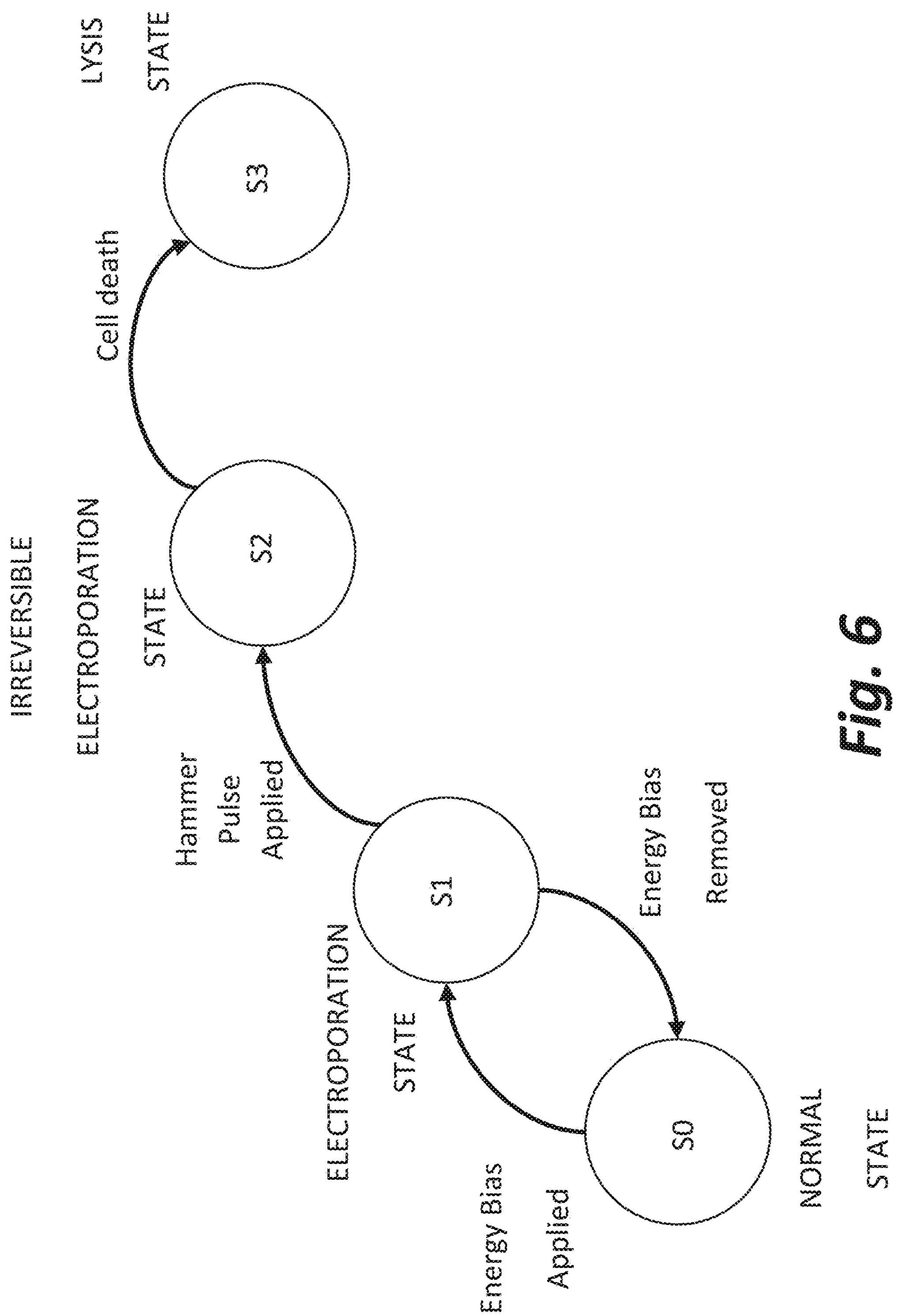
FIG. 6 depicts a state machine of PFI according to the disclosure.

FIG. 6 depicts the state machine of PFI. The system starts at a normal state, S0, and may jump to state S1, reversible electroporation through the biasing of the target diseased cells. S1 may be exited back down to state S0 through cell membrane closure as time passes, or through an inverted PFI pulse that will close the membrane pores. When in State S1, a hammer pulse may be applied to reach into state S2, with an additional modification to waveform parameters per methods highlighted elsewhere within this embodiment. Cells that enter this state lose integrity and transition to state S3, lysis. Within a zone, it is possible to target a combination of cells that are in rEP (reversible electroporation) and IRE, moving states across different volume zones.

Figure 7:
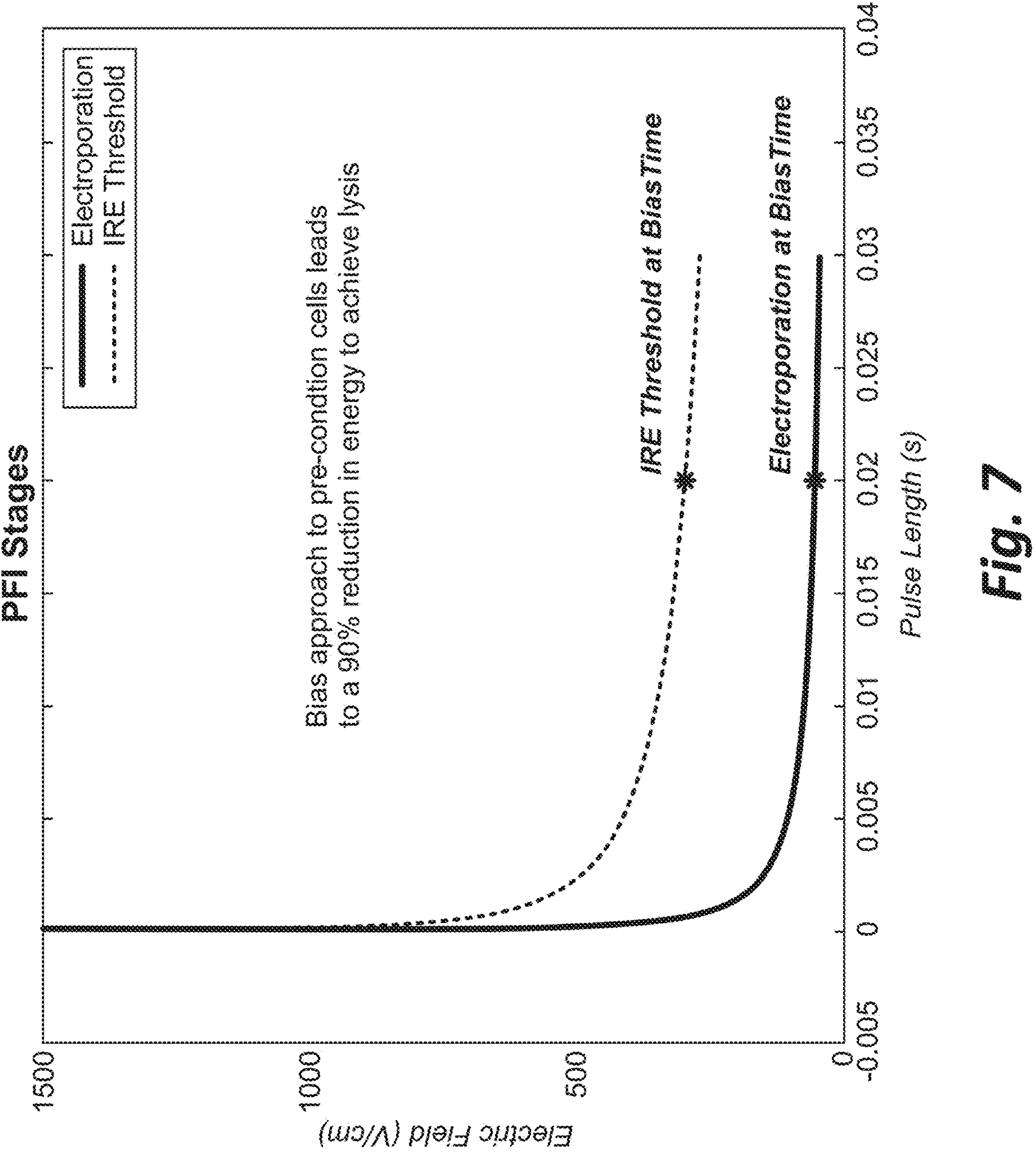
FIG. 7 depicts a simulation of electric fields needed against specified pulse durations to accomplish IRE vs reversible electroporation according to the disclosure.

FIG. 7 depicts a simulation of electric fields needed against specified pulse durations to accomplish IRE vs reversible electroporation according to the disclosure.

Figure 8:
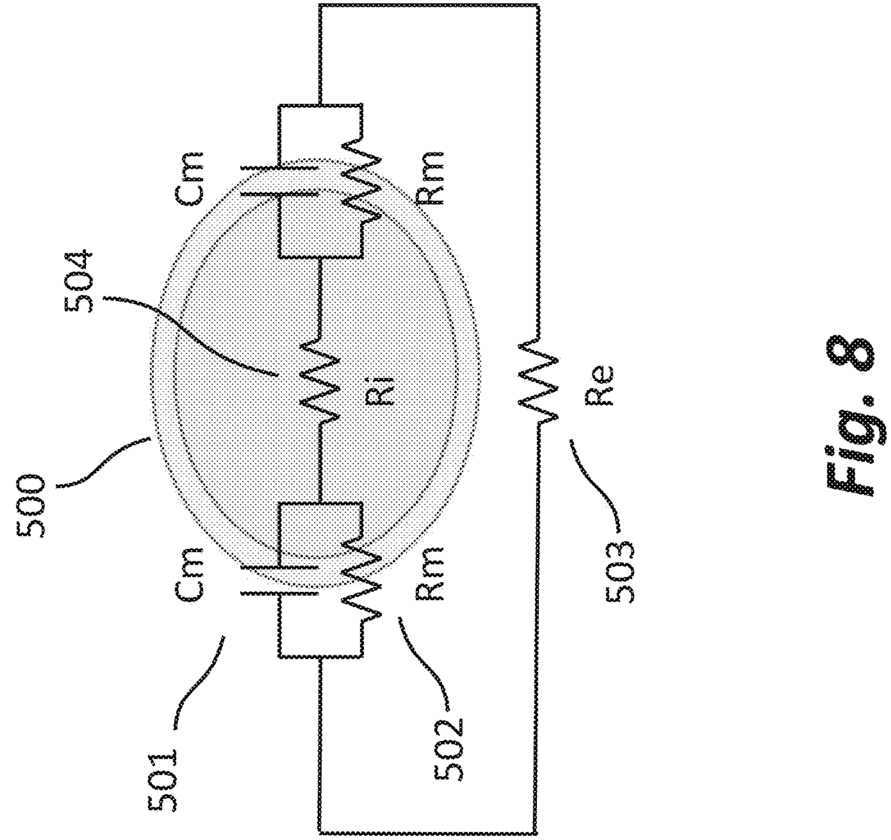
FIG. 8 depicts a tissue cell model according to the disclosure.

FIG. 8 depicts a tissue cell model item 500. The cell membrane walls have both a capacitance portion, Cm, 501 and a resistive portion, Rm, 502. Extracellular resistance 503 is body fluid (a.k.a. blood). Intracellular resistance 504 is within the cell.

Figure 9:
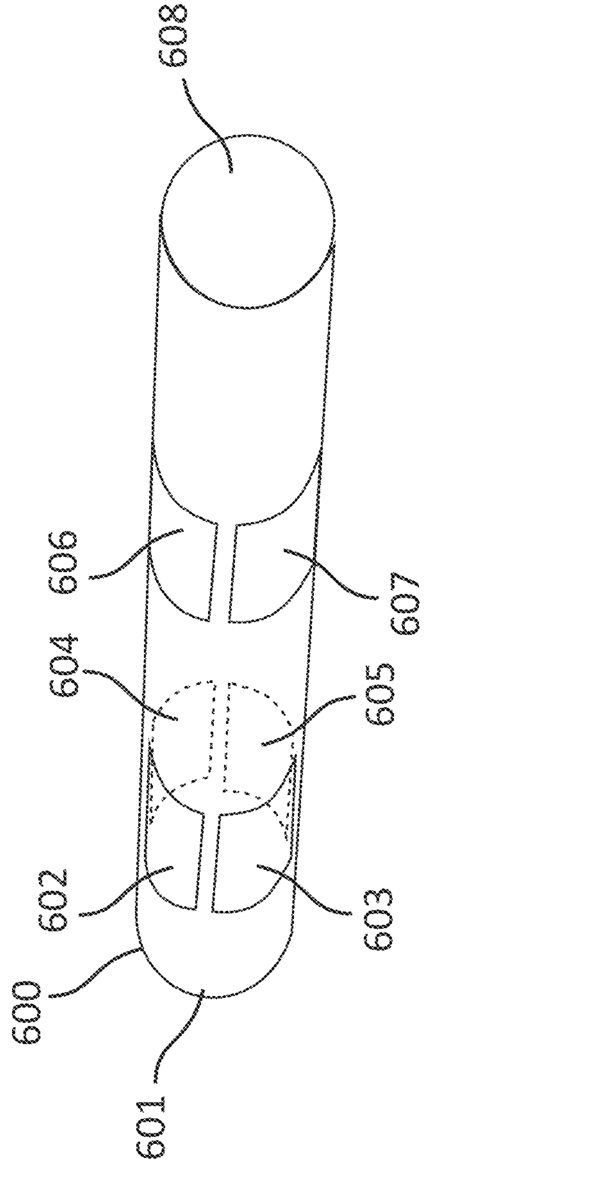
FIG. 9 depicts a PFI device applicator according to the disclosure.

FIG. 9 depicts a PFI device applicator 600. Many embodiments of the applicator may be shown. The applicator is comprised of a round, pointy, sharp, or dull tip 601. This may help navigate the placement of the applicator and may change per accessibility demands of the target zone/cancer type. Two or more groupings of electrodes are placed within the electrode. A distal electrode group 602, 603, 604, and 605 are shown in the example as a four-quadrant embodiment, however, two or more zones may be created per group. The example shown has two groups (proximal and distal), but more groups may be created. A proximal group is shown 606 and 607, but only two electrodes on one side of the applicator are shown—the other two electrodes are implied to be on the back side (non-transparent drawing). As with the distal, there may be more than two electrode groups with the intention of creating directional fields within the body. The applicator continues along item 608 per a standard catheter design.

Figure 10:
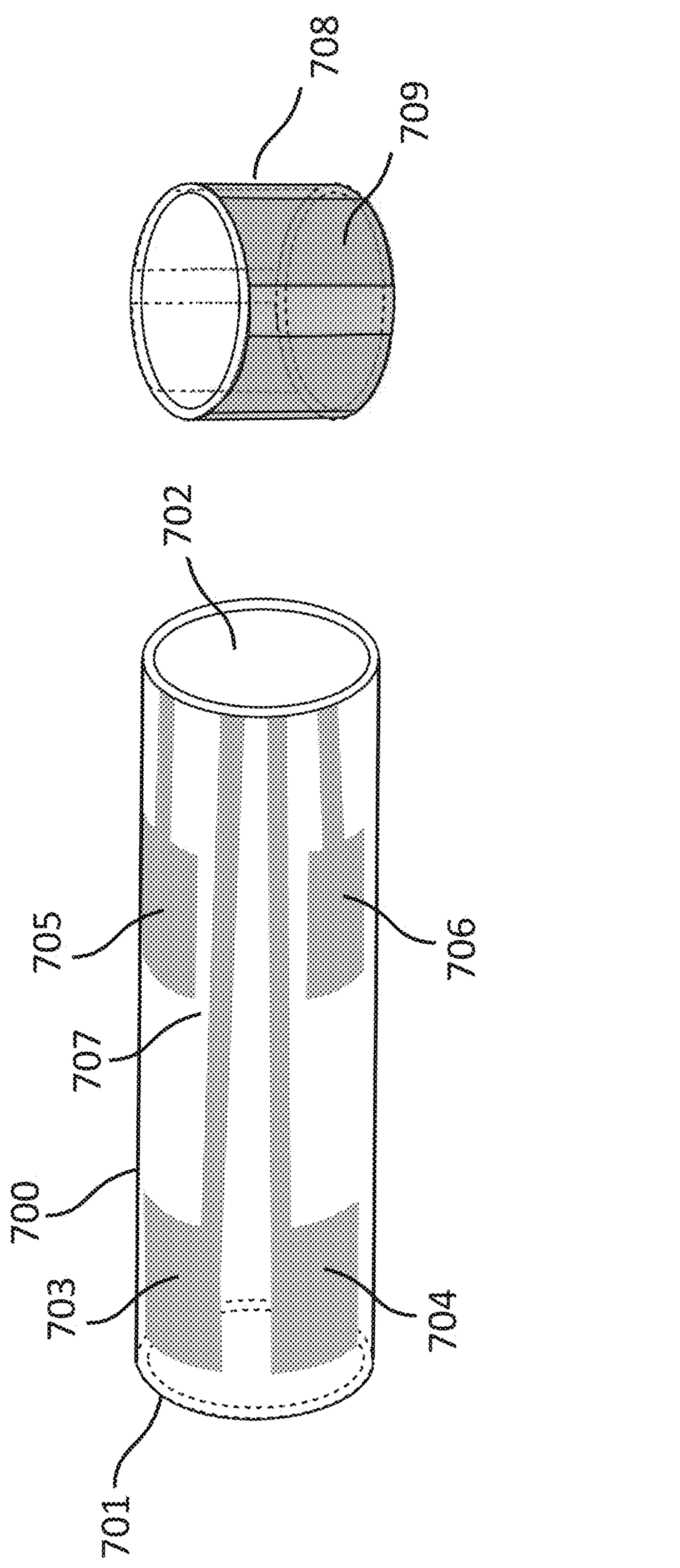
FIG. 10 depicts one possible embodiment of manufacturing of a PFI applicator according to the disclosure.

FIG. 10 depicts one possible embodiment of manufacturing of the applicator 700. This embodiment shows electrodes 703, 704, 705, and 706 etched onto a substrate (i.e. ceramic, or plastic). Channels 707 are created through the etching design, which allows for signals to be routed through for assembly purposes. Paralyne (or other) coating may be used to cover the exposed traces to isolate signals from each other. This may benefit electron density to control impedance measurement tolerances, as well as enabling the manufacturing process. Items 701 and 702 are the cross-section cut-outs for the applicator electrode. Item 708 shows a see-through diagram of a cross-section of electrodes 709 to show they are evenly spaced out as one potential embodiment. Wires are connected to the plated electrodes as a similar method to traces being run on the substrate. Other manufacturable implementations exist and may blend a multi-zone distal or proximal (or more bands in-between) that connect welded ultra-thin wires to the electrode zones.

Figure 11:
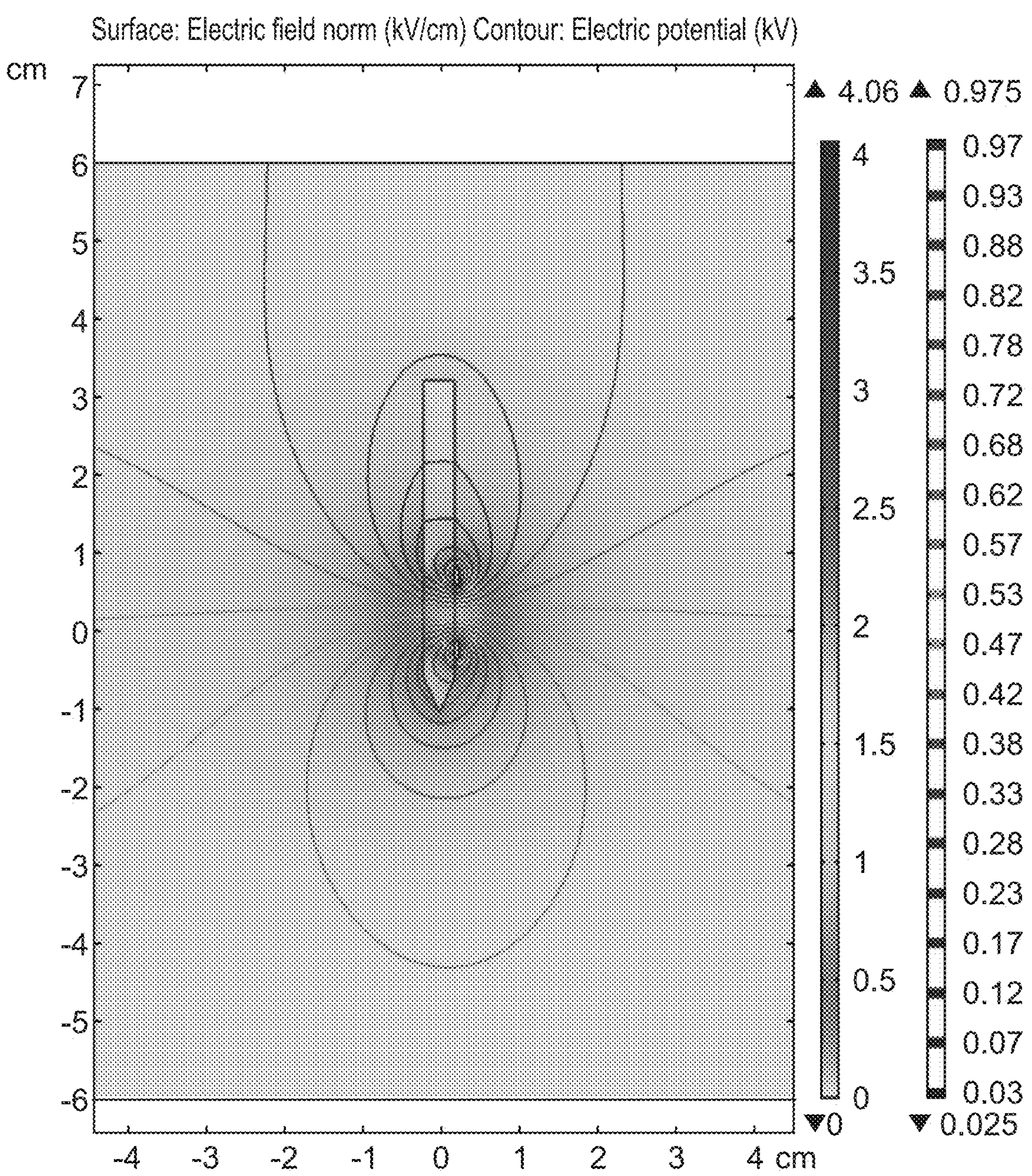
FIG. 11 depicts an electric field simulation of a simple applicator according to the disclosure.

FIG. 11 depicts an electric field simulation of a simple applicator to look for appropriate kV/cm as an example embodiment to assess performance.

Figure 12:
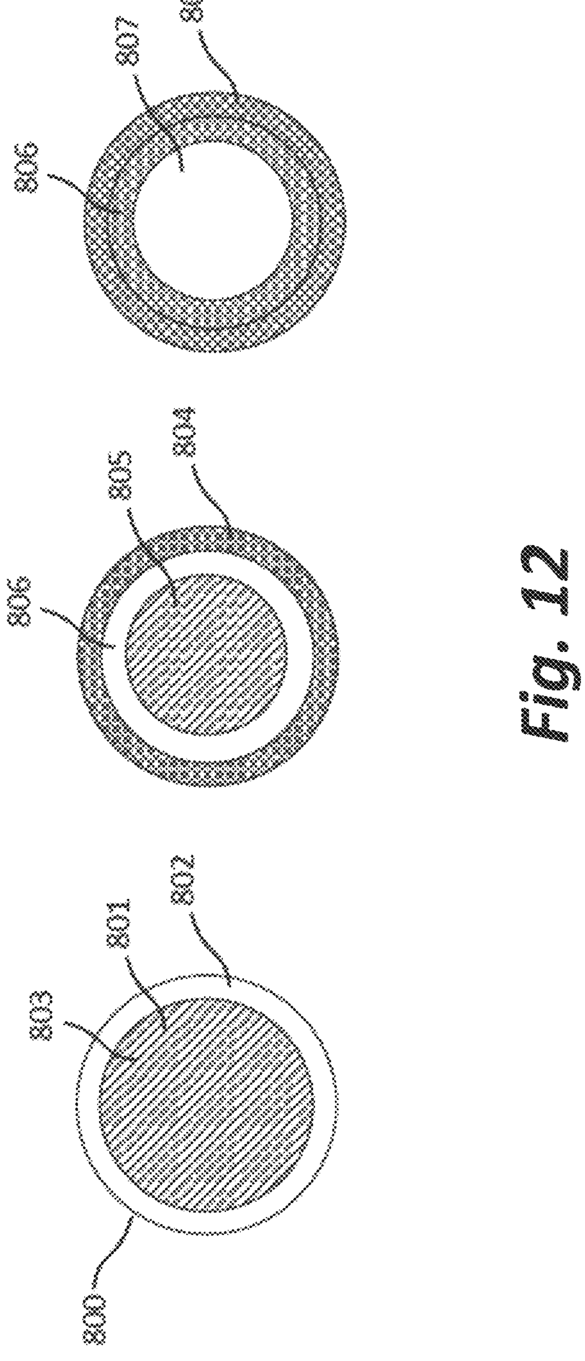
FIG. 12 depicts a method of shells/volumetric zones and how to use switching of cell membrane states according to the disclosure.

FIG. 12 depicts a method of shells/volumetric zones and how to use switching of cell membrane states (described in FIG. 6) in a novel way. In an example cell 800, a volumetric zone of reversible electroporation (rEP) 801 is created which is a sphere of target tissue. Irreversible electroporation (IRE) is then created to target a larger 'shell' outside of the rEP volumetric zone 802. The rEP volumetric zone 803 returns to normal non-pore cell membrane either through time (a natural cell membrane closing process) or through an inverted rEP pulse to close the cell membranes. In this case the bias of FIG. 4, which is the initial start of the waveform is also inverted after the hammer pulsing has occurred. The amplitude, slew rate, pulse frequency and the mixed bias/hammer pulse all play a critical role in this method. Once the rEP volumetric zone 803 has reverted, the next shell may be created. Establishing that a larger volumetric zone of IRE 804 is present, a new rEP volumetric zone 805 is created that is smaller than the first rEP volumetric zone. The new IRE volumetric zone 806 is created through the hammer pulses. Two volumetric zones have been treated at this point 804 and 806. Reversion occurs on item 805 and the method repeats on volumetric zone 807 until the full volume has been treated. Volumetric zone creation has a range of electric fields density that enables a thickness of zones to be created and this may be dialed in for fine-tuning of an embodiment.

Pulse Field Immunotherapy (PFI)

The PFI disclosed herein utilizes a novel irreversible electroporation (IRE) waveform optimized to preserve as much intracellular contents as possible. This is best understood by first starting with the normal states the system may achieve on a cellular level, shown in FIG. 6. Along with this figure, the proposed waveforms shown in FIG. 4 demonstrate the concept. This figure shows item 30, a time-series plot, that constructs a waveform capable of PFI. In practice, an optimization based on different tissues will occur per the TIP module, with local immune cell activation through electrical pulses or activation of the vagus nerve, allowing for further optimization. Note similar waveforms may be constructed by applying electric fields on the Y axis and time on the X axis.

FIG. 4 shows a controlled rise in voltage with respect to time 32. Per cell models, shown in FIG. 8, there is both a high frequency and low frequency element of a cell, hence the rise/fall times of the pulse must be controlled. If not controlled, the AC model of the tissue cell places more energy to the intracellular contents 504. The bias dwell time 34 uses the voltage level of the bias 33 to achieve electroporation. This creates pores within the cell membrane. A targeted hammer pulse 35) with controlled rise time and voltage characteristics 36 target the cell membrane 501 and 502. The pulses repeat a certain number of times 37 to probabilistically capture a large portion of the localized tissue for PFI. The final biasing of remaining cells captures current 503 and voltage 504 to confirm tissue complex impedance, followed by the bias being turned off 38. This will have a new TIP that results in a lysis mixture, confirming that the tissue was appropriately treated. Note that the unique waveform pushes targeted cells into different states to accomplish a reduced heating lysis phenomenon.

These concepts work on a larger scale as target areas increase through multiple centimeters of tumors. Although this example embodiment is an architype for pancreatic cancer, these concepts lend themselves to multiple other cancers, for example breast and prostate.

Additionally, drugs may be added to help further target the membrane and may be added to target preservation of the antigens. Some drugs may be added to better allow access for the immune system to target the antigens after the immune system has been trained.

FIG. 5 shows a block diagram of an exemplary PFI generator. The TIP circuit/device can be removed from a base-generator to reside in a secondary system.

FIG. 7 shows a model of the behavior of lysing through electroporation, and an expected IRE threshold. The energy needed to perform IRE across 1 cm is 300V. At 20 ms, assuming 3 cycles and 3 packets delivered to allow time for the heat to dissipate, this yields 108 joules, assuming patient impedance is 150 ohms. The equivalent approach with a PFI approach is to bias the cells across 1 cm with a 20 ms pulse that is 50V to get electroporation to occur. Once in this state, a 10 kV pulse is used to hammer the cells and take them well into the lysis state. The total energy used with this approach is ~10 joules. This is a 90% reduction in heat, which helps preserve the intracellular contents. Other PFA approaches may use up to 2,000 joules of energy to accomplish the desired treatment necessitating the delivery of therapy over the course of minutes/hours to attempt to control heat/prevent thermal ablation, which increases the likelihood of procedure complications.

Induced transmembrane voltage (ITV) can vary with size and direction which plays into thermal and non-thermal damaging of cells.

It may be possible to cause cell lysing through changing the angle of the electric field abruptly. This involves physical separation of electrodes. Where a pore is formed through electric field formation on one angle and a separate electric field is created at a different angle, in close proximity to the first one, but much more aggressively. This may create two pores and increases the probability of membrane collapse, with minimal heat utilized. For cells that are growing/replicating internally, an increase in pores may have a lower threshold of electric field required for lysing.

To further minimize unnecessary heating of the target tissue (which may kill the cells), an alternative or augmented shell method can be used in conjunction with the bias/hammer pulses, and is shown in FIG. 12. This method starts at the outer-most shell 802 by creating a reversible electroporation zone 801. This zone creates pores, which expose the inner cell resistance. This may drop the overall resistance of the cell to create a Thevenin equivalent circuit with body fluid (blood). A second pulse (the hammer pulse) will target IRE beyond the threshold of zone 801. Cells are allowed to recover at 803. The process repeats with smaller peak voltages to target a smaller lesion size—a new rEP zone 805 is created and an IRE extension 806 is created and so forth until the desired lesion is fully filled in. This may work to eliminate or minimize thermal ablation within the tumor. This leverages pore creation, creating an electrical path (and hence impedance change) through the cell, vs forcing the hammer pulse into the membrane, which may yield IRE. The possibility of creating a voltage potential of 1V across the cell to destabilize it may work beneficially against not destabilizing the intracellular contents due to their smaller size. This method is non-obvious as it must convert IRE in the reverse order and allow a resting time for rEP cells to return to normal, which can be optimized through monitoring impedance return to baseline levels. Note there may be a relation to achieve IRE fields of targeted areas against specific cancer cell sizes (10-200 um), which will help target a specific cancer based on cell size, which is a further embodiment of PFI enabled through TIP feedback augmentation of the waveform to target zones of shell voltages for a detected cell type.

Tissue Identity Profiles™ (TIPs)

The sensing portion of the disclosure will aid with real time diagnoses of different tissues. This ranges from early cysts to advanced cancers, including (but not limited to): pseudocysts, serous cyst, IPMN, MCN, prevailing cancers (e.g. adenocarcinoma, and neuroendocrine tumor). The sensing works hand-in-hand with FNA, which will be used to further identify tissue properties observed in patients against measurements, henceforth referred to as Tissue Identity Profiles (TIP's). As the library of TIP's increases, confidence increases with identification within patients, better decisions can be made in real time. FNA sampling is left as an option to the practitioner, however, reducing the cancerous material from a tumor reduces the potential for creating a PFI response (less antigens for the immune system to react against).

At the clinician's discretion, pseudocysts and serous cysts may be left alone with a backing of FNA for confirmation. This is an important advantage-NOT performing an FNA preserves additional antigens in-place within the tumor's location, improving the likelihood of PFI to occur once treatment is applied. Further, FNA on rare occasions can cause tumor seeding whereas the biopsy dislodges and spreads cancer cells. IPMNs and MCNs have malignant potential and may be treated on the spot with PFI as a preventative measure, at the clinician's discretion. Tissue identified as diseased using the TIP may be treated immediately due to their malignancy. This may provide an alternate to surgery and is treated as soon as detection is made-earlier treatment has been noted to be key to improve outcomes.

Measurements made to create the TIP include capacitance, voltage (magnitude), phase, and others. Ranges pF to nF measurements, for example (but not limited to), but may be further reduced, which means very low electrode/probe capacitance is needed, or alternately calibrated out of the Thevenin equivalence. Likewise, uV ranges are expected, but may be more granular as the need arises. Frequency domain analysis can be performed on all data to look for patterns and bin tissue types. Several types of data processing can be applied here to help identify the exact tissue type. For example, performing a Fast Fourier Transform (FFT) may provide different responses unique to a specific tissue. Other data processing may likewise yield identifiable results.

Sensitivity of area of the probe may be needed to achieve a minimum surface area for electron density of the probe. Cable length and probes may need to be specified and maintained in a production environment within a specified tolerance range. This means material properties of the applicator (a.k.a. catheter/probe) may be essential.

A bus and memory connection, shown in FIGS. 5, 417, 418, and 419, show a means of storing the detected TIP and passing this information to the controller board 410. Additionally, different patients have different impedances, so a measurement of the normal patient impedance will be used, acquired through device/cathode connector 401. TIP identifications may be normalized or go through a transform based on different patient impedances. This is part of the novel algorithm that makes the TIP extraction unique and may improve accuracy of tissue identification from patient to patient. Furthermore, identification of a specific tumor or cancer will help provide information on the size of the tumor and therefor empower the PFI therapy to adjust the appropriate therapy size, minimizing heating while appropriately dialing in necessary parameters to perform lysis on a target zone.

Machine learning can be implemented through use of uploading TIPs and FNA correlation to a cloud-based database and does not need to include protected health information (PHI) or patient identifiable information (PII). This is a valuable look-up database that can be formed and helps to solidify a library of relevant data to improve outcomes to distinguish between multiple types of tissue (e.g., healthy, already treated tissue, tumors, non-malignant tumors, i.e. diseased tissue, etc.). Additional algorithms, such as normalizing against patient impedances/TIPs, with respect to different medications patients may be prescribed, can also be implemented to further refine the TIP.

Field Form Catheter (Applicator)

The use of an applicator that can create multiple phases of vectors may aid in fully capturing different polarities of cell membranes. This is unlike traditional ring electrode catheters as the electrodes are placed in different segments around the main shaft of the catheter. FIG. 9 shows an example physical layout. In the depicted embodiment, there are two main electrode bunches—a proximal and a distal, however, in practice, there could be two or more to increase resolution of fields and balance manufacturing capabilities across vendors. Each bundle in this figure shows four quadrants, however, there could be more or less than four quadrants. The distal portion of the applicator is shown to have 4 quadrants 602-605 for example. Only two of the four electrodes 606 & 607 are shown on the drawing for the proximal portion of the applicator. This provides a novel capability to add changing vectors within the body without having to re-position the applicator. This also provides the possibility to enable directional control PFI by changing the vector of the field applied to the cells, as mentioned with the complete system use, which may further enable lysis of the cells with less overall energy. Additional vectors (combining different electrodes on different sides of the applicator) may provide a novel enhancement of determining different tissue characteristics to further refine the TIP.

This embodiment of the applicator can change the angle of fields (the vector is typically measured in V/cm or kV/cm) with the aim of improving the efficiency of lysing the cells. The configuration of the electrodes on the applicator may also allow the ability to sense the characteristics of the tissue that will provide an indication of when lysing is occurring and for the categorization of different TIPs. This information could be used to create a mappable zone of the tissue to form several TIPs within the localized electrode placement by sensing different electrodes. Furthermore, varying the impedance measurement voltage will penetrate deeper into the tissue and may help see near and far tissue volume impedance effects, allowing for a 3D impedance shell map to be formed. This may further help with PFI verification as the multiple cell states (normal, rEP, and IRE) can be measured as the shells penetrate deeper tissue.

FIG. 10 shows a method of fabrication of the FieldForm electrodes. This method embeds conductive electrodes on the surface of a circular substrate, for example, ceramic, plastic, or glass, with parylene coating masking the non-electrode areas. Electrodes can be alternated such that clearance is maintained between signal polarities. During therapy, nearby electrodes are electrically floated. This may be as simple as two proximal and two distal electrodes, but this embodiment shows 4 distal and 4 proximal. Floated electrodes may intermittently connect through the TIP generator to perform measurements while high voltage is not being generated. The FieldForm electrodes may be on several different electrode/catheter configurations, for example, (1) a hollowed needle tip, (2) a pointed non-hollow probe tip, (3) a catheter electrode with various ends, for example a strain gauge end to determine insertion or tissue pressure. Other examples exist. Additional manufacturing methods exist that can leverage a more traditional electrode, now enhanced with zones surrounding the axis, or furthermore a small circular substrate that is spot welded with wires as a distinct section of the applicator groups—numbering 2 or more (e.g. proximal, distal, one or more on the inner area between proximal and distal).

FIG. 11 shows the kV/cm FEA simulation in tissue that may start to lead to a validated model. This shows a probe with only two electrodes printed on a ceramic needle embedded in tissue. The main observation is direct control of the E field—currently looking like 1 kV per cm.

Some embodiments may be able to use a sonic endoscope to delivery PFI energy, others may just use the applicator with a sharp tip (e.g., a needle electrode), directly administering PFI into a tumor.

A number of advantages are provided by the embodiments set forth herein, as set forth below.

Pulse Field Immunotherapy (PFI)

The use of PFI vs existing PFA therapies may reduce damage to the intracellular contents, e.g., preserving as much antigen as possible, which may improve immunotherapy results.

The use of PFI vs existing PFA therapies may reduce or eliminate thermal heating zones, contributing to preservation of intracellular content and reducing damage to healthy tissue and structures in the vicinity of the treatment zone.

The use of PFI with additional drugs may further improve the immune response.

The use of PFI does not involve other more detrimental methods, e.g., chemotherapy.

The use of PFI progressions through biasing to different stages may allow for IRE with less thermal heating.

The use of the customized waveforms with different states allows the cells to stabilize in the reversible electroporation state (rEP), and then as the hammer pulse is applied with a different vector/angle, the channels that have formed may pull on the cell membrane like a zipper, destabilizing the membrane. They may also form new larger pores, which in combination with the pre-existing pores with a different vector, may destabilize the membrane into collapsing. The FieldForm applicator can help to change the direction of the fields, working in conjunction with the initial bias pulse for establishing the reversible electroporation state.

The use of customized waveforms (the biasing and hammer pulses) establishing different states allows for shells to be formed, allowing for IRE targeting on the external fringe with safely transitioning more centralized cells to rEP, such that an improved thermal performance with IRE is established. This action takes advantage of the natural lower impedance of the intracellular contents, but may not break up intracellular content due to a lower voltage being exposed across the cell boundary, preserving it. An rEP, IRE, and inverted-rEP waveform combination may further reduce procedure time with the benefits of PFI.

Tissue Identity Profiles (TIPs)

From the immediate feedback of TIP's, the clinician/practitioner will know if diseased tissue is present and can make an immediate decision to perform PFI treatment, reducing the procedures the patient must undergo to just a single procedure for both diagnosis and treatment.

As shown in FIG. 3, item 24, when a TIP already exists, this allows for the practitioner to make the assessment to skip performing an FNA. FNA's reduce the volume of the cyst or tumor, which may work against PFI as cell material is removed. While FNA can still be taken, leaving the most antigens in situ may help provide a larger signal to the immune system to activate.

FieldForm Catheter (Applicator)

The FieldForm catheter creates multiple polarized directions for current to flow, which may improve PFI results and target different areas (in the case of asymmetric body or tumor structures with respect to the placement of the applicator within the body).

The FieldForm catheter creates multiple electrodes to sense different regions of tissue for TIPs which may improve feedback for PFI confirmation. Multiple electrodes may provide optimal immune cell activation points, which may improve PFI further. A separate applicator could be used to enhance immune response while PFI is being delivered. The systemic immune response at different locations in body may be activated by stimulating Cranial Nerves like Olfactory nerve (CN I), Optic nerve (CN II), Vagus nerve (CN X) or Spinal nerves using immune stimulating pulse (ISP). The immune enhancing pulse frequency may be from 0.05 Hz to 10 MHz where amplitude could be anywhere from 0.1 V to 300 V.

This present application covers systems, devices and methods with several different embodiments that may have substantial benefits.

In embodiments, the disclosure provides for electrically pre-biased tissue with phased irreversible electroporation low-energy pulses for tissue ablation, achieving pulse field immunotherapy. Thus, methods, devices and systems for reduced muscle stimulation with phased irreversible electroporation for tissue ablation and pulse field immunotherapy are disclosed. In such embodiments, tissue can be pre-biased with a voltage and allowed to settle. A hammer pulse with various characteristics riding on the bias voltage can then be injected. This will have a different phase, frequency, and amplitude than the bias pulse. The reduced biasing may have less effect on muscle stimulation than what has been clinically shown for existing PFA therapies. The reduced number of pulses vs existing PFA therapies may have a significant thermal benefit. The pulse may still yield an IRE effect, with less heating due to the lower bias point, but the cell membrane may still rip apart irreversibly due to the higher potential across the cell. Different angles of electric fields may create an improved PFI result by putting the cell membrane under different vectors of stress. Utilizing the natural rEP and IRE shells, this may create an improved thermal zone, with fewer pulses to improve the overall lesion size. Applying an rEP-IRE-inverted-rEP pattern may further shorten procedure duration.

In embodiments, methods, devices and systems for identification of tissue are provided. During insertion of the catheter into the body, Essential Characteristics (EC's) are monitored at a substantially fast frequency. EC's can include, but are not limited to impedance taken across a range of frequencies, monitored voltage magnitude, phases, and capacitance across a range of frequencies. Upon entry into a tumor, the characteristics of the tumor are logged and stored as a profile, including impedance at different frequencies and capacitance at different frequencies. The profile is stored as part of a growing record of tumor types. All encountered tissues are stored as part of a Tissue Identity Profile (TIP) that enhances identification of tumors.

The TIP sensing system is paired with an IRE, PFA, or other system to augment existing systems, but may be built into a pre-existing system. Therapy is delivered and the tumor cell characteristics are measured again using the TIP sensing system. With this information, a determination that IRE of the targeted tumor cells is complete could be used to discontinue therapy reducing overall therapy delivery time. The system, when used with a multi-electrode delivery system may provide profile performance across distance to help determine both tumor and ablation sizes. Machine learning/Artificial intelligence may be used to help characterize and determine appropriate therapy vs treatment across a population.

In embodiments, methods, devices and systems for reduced energy irreversible electroporation with multiple electrode delivery are provided. Such embodiments are similar to the methods, devices and systems for reduced muscle stimulation with phased irreversible electroporation for tissue ablation and PFI as described above, but may utilize pseudo-random frequency and voltages sent to the catheter electrodes. Different vectors can be created through the randomness to lysis the cells more quickly. Each paired electrode path piecewise integrates the thermal expected temperatures, to avoid overheating. The algorithm can shift weighted field direction to compensate for non-symmetrical tissues, based on directional impedance measurements. The algorithm uses feedback from TIPs to adjust direction and voltages to ensure appropriate and minimal therapy has been performed.

In embodiments, methods and devices (e.g., catheter) for electric field shaping are provided. Such embodiments can include a catheter/device/applicator with multiple zones or quadrants (for example) of electrodes for directional therapy and sensing. An algorithm workflow can be utilized to create polarized vectors across multiple zones/quadrants. In one embodiment, the applicator can have multiple zones of electrodes with four quadrants per zone. In other embodiments the electrodes may not be four quadrants, it could be two and six quadrants, for example.

In embodiments, tissue ablation with electrically pre-biased tissue with polarizing magnetic resonance for PFI is provided. Such embodiments are a potential alternative to lysing cells as described above. The tissue can be pre-biased with a voltage and allow to settle. As soon as electroporation is established, a strong localized magnetic field can be created around the cells, further stressing the targeted cells. The additional cellular stress may cause a further reduction in energy required for IRE. This approach, with reduced pulse intensity and energy delivery time may also reduce muscle stimulation.

According to various embodiments disclosed herein, a system can be provided to identify tissue and automatically adjust pulse electric field therapy. The system can include a PFI generator, a processing unit, a catheter/applicator and a tissue identification sensor. An immune excitation module can further be added. The system can work with pre-existing ultrasound catheters. The tissue identification sensor can collect data, which is sent to the processor unit. The processing unit can analyze the data and adjust signals of the PFI generator to adjust the therapy. The processing unit can control the immune excitation generator to apply signals at the appropriate time. The system can receive electrical tissue data from the inserted catheter electrode(s) and may receive inputs from a field clinical engineer on what the type of tissue is that the sensor is currently inserted into. The system can output an electrical sweep of signals to the catheter, pulse field immunotherapy signals, with the intent of exposing intracellular content to the immune system, immune excitation waveforms to activate the immune system to enhance the ability of creating an immune response and can provide real-time data to a user interface for monitoring. In embodiments, the system can be automated but allow for user inputs to adjust for desired lesion size.

In embodiments, the output waveform can be actively adjusted based on the type of tissue that it has detected to help create an immune response.

In embodiments, immune excitation signals can be delivered post-therapy to further evoke an immune response.

In embodiments, the catheter can use multiple electrodes to help form fields, allowing for an enhanced therapy to occur.

In embodiments, system can use the catheter with feedback to lyse zones of cells.

In embodiments, the system can use a method and feedback to show cells are electroporated, and then apply an irreversible electroporation waveform.

In embodiments, a medical system for delivering therapy energy to tissue can include an output configured to deliver patient therapy to one or more applicator or catheter electrodes. The output can be configured, tuned, or managed to maximize cellular extraction and preservation of antigens from malignant tumors. The system can further include a pulse field immunotherapy (PFI), pulse electric field (PEF), pulse field ablation (PFA), or other high voltage transient circuit/generator/module device. Such device can include one or more modules allowing waveforms to generate PFI pulses, one or more low/medium/high voltage supply generating circuits, one or more transient or H-bridge generating circuits, a switching circuit capable of blending voltage levels to generate PFI pulses and one or more processors configured to manage aspects of PFI therapy.

In an embodiment, a medical system for delivering pulse electric field therapy energy to tissue can include a pulse field immunotherapy generator configured to generate therapy pulses. An applicator with one or more electrodes can be configured to deliver the therapy pulses to tissue. A tissue identification module can be configured to analyze data from the applicator as the applicator interfaces with the tissue. A processing unit can be configured to receive and/or analyze tissue identifications, and to generate appropriate therapy pulses based on the tissue identifications. One or more user interfaces can be configured to display the tissue identifications and allow user inputs to adjust desired lesion size or other therapy parameters.

In some embodiments, the pulse field immunotherapy generator is configured to first prime the tissue in a reversible electroporation (rEP) state with the therapy pulses and then to an irreversible electroporation (IRE) state.

In some embodiments, a state of the tissue can be confirmed through tissue identifications by the tissue identification module.

In some embodiments, the applicator is configured to utilize the one or more electrodes to deliver the therapy pulses to the tissue by controlling the intensity and/or volume of the therapy pulses within different volumetric zones of the tissue.

In some embodiments, more than one electrode can be used to change a direction of electric fields through commands of the processing unit.

In some embodiments, the direction of the electric fields may be adjusted based upon the tissue identifications from the tissue identification module.

In some embodiments, the pulse field immunotherapy generator is configured to first prime the tissue in an irreversible electroporation (IRE) state with the therapy pulses and then to a reversible electroporation (rEP) state.

In some embodiments, the pulse field immunotherapy generator is configured to apply an inverted reversible electroporation state to the tissue with the therapy pulses after a reversible electroporation (rEP) state is established.

In some embodiments, the tissue identification module may utilize different applicator electrode pairs to determine a state of the tissue than are used for delivering the therapy pulses to the tissue.

In some embodiments, the processing unit may configure the therapy to target different tissues based on tissue identifications from the tissue identification module.

In some embodiments, the system further includes an Immune Excitation Module (IEM) configured to activate a systemic immune response in the tissue, and the IEM is configured to be controlled by the processing unit before or after the therapy pulses are delivered.

In some embodiments, the pulse field immunotherapy generator is configured with different sequences of application of the IEM, including before irreversible electroporation (IRE), after IRE, or before/after reversible electroporation (rEP) or inverted-rEP therapy pulses are delivered.

In some embodiments, the IEM is configured with pulse frequency ranges from 0.05 Hz to 10 MHz and amplitude from 0.01V to 300V.

In some embodiments, the pulse field immunotherapy generator is utilized in addition to drugs that aide the preservation of antigens and/or other internal cellular contents.

In some embodiments, the pulse field immunotherapy generator is utilized in addition to drugs that aid destruction of malignant tissue.

In some embodiments, the pulse field immunotherapy generator is utilized in conjunction with a database of known tissue measurements to extrapolate and augment tissue identification by the tissue identification module.

In some embodiments, the database of known tissue measurements resides on a cloud server or locally within the pulse field immunotherapy generator to make tissue identification commonly available to enhance treatment options and/or to allow for machine learning to improve pulse field immunotherapy.

In an embodiment, a method for performing pulse field immunotherapy (PFI) with an electroporation device can include applying one or more PFI pulses to one or more volumetric zones of tissue. Different therapy pulses can be applied to change a cell membrane state in the one or more volumetric zones of tissue. Therapy pulses can be applied to different electrodes on an applicator to change a direction vector of an electric field. The cell membrane states can be detected in the one or more volumetric zones of tissue through a tissue identification module to determine the cell membrane states.

In some embodiments, the different therapy pulses include reversible electroporation, inverted reversible electroporation, irreversible electroporation, inverted irreversible electroporation, and other intermediate electroporation states or transition phases.

In some embodiments, each application of therapy pulses targets a specified volumetric zone of tissue.

In some embodiments, targeting volumetric zones of tissue can start with a largest sphere and decrement down to a smallest resolvable sphere.

In some embodiments, targeting volumetric zones of tissue can start with a smallest resolvable sphere and increment up to a largest resolvable sphere.

In some embodiments, tissue identification allows for cell membrane state to be determined to optimize percentage of tissue that has entered a new state.

In some embodiments, tissue identification allows for cell membrane state to optimize the time spent applying therapy pulses to a targeted volumetric zone.

In some embodiments, targeted volumetric zones of different applied therapy form multiple layers of shells within the total volumetric largest sphere to systematically treat targeted tissue.

In some embodiments, an amplitude, slew rate, pulse frequency and mixed bias therapy pulse can be adjusted to preserve antigens/intracellular content and/or previously recorded tissue identification settings.

In some embodiments, the targeted volumetric zones of different applied therapy have a mixed time base signal with large energy differentials.

In an embodiment, an electroporation device for delivering pulse field immunotherapy pulses can include an electroporation module configured to generate therapy pulses, a plurality of output channels, including one or more capable of simultaneous usage and a plurality of input channels, including one or more capable of simultaneous usage. A tissue identification module can be configured to identify tissue from one or more input/output channels. One or more processing units can control appropriate therapy. A mixer can be capable of combining channels from the plurality of input/output channels to identify tissue, provide therapy, or connect application-specific functionality, and further include an ability to add modules to utilize channels for application-specific functionality.

In some embodiments, combined channels can be within a voltage range of 100V to 25 kV. In some embodiments, combined channels can overlap and have a pulse duration of 100 ns to 500 ms with a mixed pulse of Ins to 100 ms.

In some embodiments, combined channels can originate from one or more different channels.

In some embodiments, combined channels can be monopolar, bipolar or both.

In some embodiments, the processing unit is capable of mixing different modules.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112 (f) are not to be invoked unless the specific terms "means for" or "step for" are recited in a claim.

The invention claimed is:

1. A medical system for delivering pulse electric field therapy energy to tissue, comprising:

a pulse field immunotherapy generator configured to generate therapy pulses;

an applicator with one or more electrodes configured to deliver the therapy pulses to tissue;

a tissue identification module configured to analyze data from the applicator as the applicator interfaces with the tissue;

a processing unit configured to receive and/or analyze tissue identifications, and to generate appropriate therapy pulses based on the tissue identifications;

one or more user interfaces configured to display the tissue identifications and allow user inputs to adjust desired lesion size or other therapy parameters; and an Immune Excitation Module (IEM) configured to activate a systemic immune response in the tissue, and wherein the IEM is configured to be controlled by the processing unit before or after the therapy pulses are delivered.

2. The system of claim 1, wherein the pulse field immunotherapy generator is configured to first bias the tissue in a reversible electroporation (rEP) state with the therapy pulses and then to an irreversible electroporation (IRE) state.

3. The system of claim 2, wherein a state of the tissue can be confirmed through tissue identifications by the tissue identification module.

4. The system of claim 3, wherein the applicator is configured to utilize the one or more electrodes to deliver the therapy pulses to the tissue by controlling the intensity and/or volume of the therapy pulses within different volumetric zones of the tissue.

5. The system of claim 3 wherein more than one electrode can be used to change a direction of electric fields through commands of the processing unit.

6. The system of claim 5, wherein the direction of the electric fields may be adjusted based upon the tissue identifications from the tissue identification module.

7. The system of claim 1, wherein the pulse field immunotherapy generator is configured to first bias the tissue in an irreversible electroporation (IRE) state with the therapy pulses and then to a reversible electroporation (rEP) state.

8. The system of claim 1, wherein the tissue identification module may utilize different applicator electrode pairs to determine a state of the tissue than are used for delivering the therapy pulses to the tissue.

9. The system of claim 1, wherein the processing unit may configure the therapy to target different tissues based on tissue identifications from the tissue identification module.

10. The system of claim 9, wherein the pulse field immunotherapy generator is utilized in conjunction with a database of known tissue measurements to extrapolate and augment tissue identification by the tissue identification module.

11. The system of claim 10, wherein the database of known tissue measurements resides on a cloud server or locally within the pulse field immunotherapy generator to make tissue identification commonly available to enhance treatment options and/or to allow for machine learning to improve pulse field immunotherapy.

12. The system of claim 1, wherein the pulse field immunotherapy generator is configured with different sequences of application of the IEM, including before irreversible electroporation (IRE), after IRE, or before/after reversible electroporation (rEP) or inverted-rEP therapy pulses are delivered.

13. The system of claim 1, wherein the IEM is configured with pulse frequency ranges from 0.05 Hz to 10 MHz and amplitude from 0.01V to 300V.

14. The system of claim 13, wherein the pulse field immunotherapy generator is utilized in addition to drugs that aide the preservation of antigens and/or other internal cellular contents.

15. The system of claim 13, wherein the pulse field immunotherapy generator is utilized in addition to drugs that aid destruction of malignant tissue.

16. The system of claim 1, wherein the IEM is configured to deliver electrical pulses to activate the systemic immune response.

17. The system of claim 1, wherein the pulse field immunotherapy generator is configured to apply therapy pulses in a pattern comprising reversible electroporation (rEP) followed by irreversible electroporation (IRE) and then inverted reversible electroporation (inverted-rEP).

18. The system of claim 17, wherein the IEM is configured to deliver immune excitation signals at one or more of: before rEP, after rEP, before IRE, after IRE, before-inverted-rEP, and after inverted-rEP.

19. The system of claim 12, wherein the IEM is configured to be controlled by the processing unit to deliver electrical pulses before biasing the tissue to an IRE state.

20. The system of claim 12, wherein the IEM is configured to be controlled by the processing unit to deliver electrical pulses after biasing the tissue to an IRE state.

21. The system of claim 12, wherein the IEM is configured to be controlled by the processing unit to deliver electrical pulses before rEP therapy pulses are delivered.

22. The system of claim 12, wherein the IEM is configured to be controlled by the processing unit to deliver electrical pulses after rEP therapy pulses are delivered.

23. The system of claim 12, wherein the IEM is configured to be controlled by the processing unit to deliver electrical pulses before inverted-rEP therapy pulses are delivered.

24. The system of claim 12, wherein the IEM is configured to be controlled by the processing unit to deliver electrical pulses after inverted-rEP therapy pulses are delivered.

25. A medical system for delivering pulse electric field therapy energy to tissue, comprising:

- a pulse field immunotherapy generator configured to generate therapy pulses;
- an applicator with one or more electrodes configured to deliver the therapy pulses to tissue;
- a tissue identification module configured to analyze data from the applicator as the applicator interfaces with the tissue;
- a processing unit configured to receive and/or analyze tissue identifications, and to generate appropriate therapy pulses based on the tissue identifications; and
- one or more user interfaces configured to display the tissue identifications and allow user inputs to adjust desired lesion size or other therapy parameters, wherein the pulse field immunotherapy generator is configured to apply an inverted reversible electroporation state to the tissue with the therapy pulses after a reversible electroporation (rEP) state is established.

* * * * *